(12) United States Patent
Starksen et al.

(10) Patent No.: US 10,709,449 B2
(45) Date of Patent: Jul. 14, 2020

(54) SYSTEMS AND METHODS FOR VARIABLE STIFFNESS TETHERS

(75) Inventors: Niel F. Starksen, Los Altos Hills, CA (US); Joe Eder, Woodside, CA (US)

(73) Assignee: Ancora Heart, Inc., Santa Clara, CA (US)

(*) Notice: Subject to any disclaimer, the term of this patent is extended or adjusted under 35 U.S.C. 154(b) by 451 days.

(21) Appl. No.: 14/000,177

(22) PCT Filed: Feb. 17, 2012

(86) PCT No.: PCT/US2012/025756
§ 371 (c)(1),
(2), (4) Date: Feb. 24, 2014

(87) PCT Pub. No.: WO2012/112967
PCT Pub. Date: Aug. 23, 2012

(65) Prior Publication Data
US 2014/0155783 A1 Jun. 5, 2014

Related U.S. Application Data

(60) Provisional application No. 61/444,645, filed on Feb. 18, 2011.

(51) Int. Cl.
*A61B 5/00* (2006.01)
*A61B 17/08* (2006.01)
(Continued)

(52) U.S. Cl.
CPC ......... *A61B 17/08* (2013.01); *A61M 25/0054* (2013.01); *A61M 25/09* (2013.01);
(Continued)

(58) Field of Classification Search
CPC .............. A61M 25/09; A61M 25/0905; A61M 2025/09058; A61M 25/0054;
(Continued)

(56) References Cited

U.S. PATENT DOCUMENTS

| 3,656,185 A | 4/1972 | Carpentier |
| 4,042,979 A | 8/1977 | Angell |

(Continued)

FOREIGN PATENT DOCUMENTS

| WO | WO-95/15715 A1 | 6/1995 |
| WO | WO-96/39942 A1 | 12/1996 |

(Continued)

OTHER PUBLICATIONS

International Search Report dated May 30, 2012. For PCT Patent Application No. PCT/US2012/025756, filed Feb. 17, 2012, 2 pages.

(Continued)

*Primary Examiner* — Max F Hindenburg
(74) *Attorney, Agent, or Firm* — Cooley LLP

(57) ABSTRACT

Described herein are devices and methods for guide elements configured with variable stiffness, with one or more flexible portions and one or more stiff portions. The flexible portion is be used as a tensioning element of a cinchable implant to tighten or compress tissues while the stiff portion is used to facilitate the insertion or withdrawal of portions of the implant or instruments acting on the implant. The guide element is further configured to be separated or severed between the flexible and stiff portions so that a flexible portion is left within the body as part of the implant, while the stiff portion is withdrawn from the body after implantation is completed.

20 Claims, 13 Drawing Sheets

(51) Int. Cl.
*A61M 25/00* (2006.01)
*A61M 25/09* (2006.01)

(52) U.S. Cl.
CPC ............ *A61M 2025/0018* (2013.01); *A61M 2025/0064* (2013.01)

(58) Field of Classification Search
CPC .. A61M 2025/0018; A61M 2025/0064; A61B 17/08
USPC ...................................................... 600/585
See application file for complete search history.

(56) References Cited

U.S. PATENT DOCUMENTS

| | | | |
|---|---|---|---|
| 4,290,151 A | 9/1981 | Massana | |
| 4,489,446 A | 12/1984 | Reed | |
| 4,922,923 A * | 5/1990 | Gambale | A61M 25/0169 600/434 |
| 5,064,431 A | 11/1991 | Gilbertson et al. | |
| 5,117,838 A * | 6/1992 | Palmer | A61M 25/0905 600/434 |
| 5,178,158 A | 1/1993 | de Toledo | |
| 5,324,298 A | 6/1994 | Phillips et al. | |
| 5,527,323 A | 6/1996 | Jervis et al. | |
| 5,538,513 A * | 7/1996 | Okajima | A61M 25/0012 138/124 |
| 5,571,215 A | 11/1996 | Sterman et al. | |
| 5,599,326 A | 2/1997 | Carter | |
| 5,701,911 A * | 12/1997 | Sasamine | A61M 25/0905 600/585 |
| 5,718,725 A | 2/1998 | Sterman et al. | |
| 5,735,290 A | 4/1998 | Sterman et al. | |
| 5,813,996 A * | 9/1998 | St. Germain | A61M 25/0905 600/434 |
| 5,817,107 A | 10/1998 | Schaller | |
| 5,961,440 A | 10/1999 | Schweich, Jr. et al. | |
| 5,980,514 A | 11/1999 | Kupiecki et al. | |
| 6,001,068 A * | 12/1999 | Uchino | A61M 25/09 600/434 |
| 6,019,736 A * | 2/2000 | Avellanet | A61M 25/09 600/585 |
| 6,039,700 A * | 3/2000 | Sauter | A61M 25/0905 600/434 |
| 6,050,936 A | 4/2000 | Schweich, Jr. et al. | |
| 6,059,715 A | 5/2000 | Schweich, Jr. et al. | |
| 6,102,932 A | 8/2000 | Kurz | |
| 6,125,852 A | 10/2000 | Stevens et al. | |
| 6,162,168 A | 12/2000 | Schweich, Jr. et al. | |
| 6,451,026 B1 * | 9/2002 | Biagtan | A61M 25/09 600/585 |
| 6,589,160 B2 | 7/2003 | Schweich, Jr. et al. | |
| 6,723,038 B1 | 4/2004 | Schroeder et al. | |
| 6,793,618 B2 | 9/2004 | Schweich, Jr. et al. | |
| 6,908,424 B2 | 6/2005 | Mortier et al. | |
| 7,125,421 B2 | 10/2006 | Tremulis et al. | |
| 7,189,199 B2 | 3/2007 | McCarthy et al. | |
| 7,326,231 B2 | 2/2008 | Phillips et al. | |
| 7,452,325 B2 | 11/2008 | Schaller | |
| 7,618,449 B2 | 11/2009 | Tremulis et al. | |
| 8,715,205 B2 * | 5/2014 | Carter | A61M 25/09 600/585 |
| 8,790,367 B2 | 7/2014 | Nguyen et al. | |
| 2003/0032979 A1 | 2/2003 | Mortier et al. | |
| 2003/0233105 A1 | 12/2003 | Gayton | |
| 2004/0054301 A1 * | 3/2004 | Cassell | A61M 25/09 600/585 |
| 2005/0137689 A1 | 6/2005 | Salahieh et al. | |
| 2005/0216078 A1 * | 9/2005 | Starksen | A61B 17/064 623/2.11 |
| 2007/0112422 A1 | 5/2007 | Dehdashtian | |
| 2007/0265658 A1 | 11/2007 | Nelson et al. | |
| 2008/0294177 A1 | 11/2008 | To et al. | |
| 2009/0182417 A1 | 7/2009 | Tremulis et al. | |
| 2009/0222083 A1 * | 9/2009 | Nguyen | A61B 17/00234 623/2.11 |
| 2009/0276038 A1 | 11/2009 | Tremulis et al. | |
| 2010/0023056 A1 | 1/2010 | Johansson et al. | |
| 2010/0049213 A1 | 2/2010 | Serina et al. | |
| 2010/0076548 A1 | 3/2010 | Konno | |
| 2010/0100055 A1 | 4/2010 | Mustapha | |
| 2010/0198208 A1 * | 8/2010 | Napp | A61B 1/00078 606/27 |

FOREIGN PATENT DOCUMENTS

| | | | |
|---|---|---|---|
| WO | WO-97/27799 A1 | 8/1997 | |
| WO | WO-97/27807 A1 | 8/1997 | |
| WO | WO-03/105667 A2 | 12/2003 | |
| WO | WO-03/105667 A3 | 12/2003 | |
| WO | WO-2005/025644 A2 | 3/2005 | |
| WO | WO-2005/025644 A3 | 3/2005 | |
| WO | WO 2006002199 A2 * | 1/2006 | ............... A61B 1/01 |
| WO | WO-2007/145751 A2 | 12/2007 | |
| WO | WO-2007/145751 A3 | 12/2007 | |
| WO | WO-2008/028135 A2 | 3/2008 | |
| WO | WO-2008/028135 A3 | 3/2008 | |

OTHER PUBLICATIONS

U.S. Appl. No. 12/253,885, filed Oct. 17, 2008, by Serina et al.
Written Opinion dated May 30, 2012. For PCT Patent Application No. PCT/US2012/025756, filed Feb. 17, 2012, 7 pages.
Extended European Search Report dated Nov. 8, 2017, for EP Application No. 12 747 626.5, filed on Feb. 17, 2012, 6 pages.

* cited by examiner

SYSTEMS AND METHODS FOR VARIABLE STIFFNESS TETHERS

CROSS-REFERENCE TO RELATED APPLICATIONS

This application is a U.S. National Phase application under 35 U.S.C. § 371 of International Application No. PCT/US2012/025756, filed Feb. 17, 2012, which designated the United States and which claims priority to U.S. Pat. Appl. No. 61/444,645, filed on Feb. 18, 2011, the disclosures of all of which are hereby incorporated by reference in their entirety.

BACKGROUND

Guide elements are commonly used in medical procedures to facilitate passage or delivery of medical instruments and implants to various locations within the body. Guide elements include devices such as guidewires, introducers and guide catheters. These guide elements may be used to pass other devices or instruments over the guide element or through the guide element, and may be configured in a variety of lengths, diameters, and tip configurations to reflect the characteristics of the particular procedure. Typically, guide elements are configured with sufficient column strength to resist axial elongation or buckling as instruments and implants are inserted or withdrawn from the guide elements. The flexibility of the guide element may also vary. For example, a guidewire may be used to insert central venous catheters through the groin and the short distance to the femoral vein, while longer, more flexible guidewires may be used to access the heart by way of the femoral artery.

BRIEF SUMMARY

Described herein are devices and methods for guide elements used to deliver one or more devices or components to a target site, wherein at least a portion of the guide element is left in the body while the remaining portion is withdrawn from the body after delivery or deployment is completed. In addition to being used to guide or restrain the movement of other devices or instruments passed over it or through it, the portion of the guide element left in the body may be further configured to anchor or manipulate other structures of an implanted device or system. The portion left in the body is configured to separate from the portion or portions that are removed from the body. For example, one embodiment of a guide element is configured with variable stiffness, with one or more flexible portions and one or more stiff portions. The flexible portion is be used as a tether or tensioning element of a cinchable implant to tighten or compress tissues while the stiff portion is used to facilitate the insertion or withdrawal of portions of the implant or instruments acting on the implant. The guide element is further configured to be separated or severed between the flexible and stiff portions so that a flexible portion is left within the body as part of the implant, while the stiff portion is withdrawn from the body after implantation is completed. For example, the flexible portion may comprise a polymeric structure that is configured to be cut by a cutting instrument that is first inserted over a stiff portion of the guide element comprising a metallic structure.

In one embodiment, guide element may comprise a rigid proximal portion, a flexible distal portion, and an attachment portion configured to releasably attach the flexible distal portion to the rigid proximal portion. The flexible distal portion may be configured to be used as a tensioning element. In some variations, the flexible portion may have a first torsional stiffness and the rigid portion may have a second torsional stiffness that is higher than the first torsional stiffness. The rigid portion may require a greater force prior to yielding in a compression test than the amount of force a flexible portion would require. In some variations, the proximal portion may comprise a first portion and a second portion, where the first portion is more rigid than the second portion. Alternatively or additionally, the rigid proximal portion may have a higher flexural modulus than the flexible distal portion (e.g., the rigid portion may have a flexural modulus of about 10 GPa, about 17 GPa, about 29 GPa, about 60 GPa, about 65 GPa, about 140 GPa, about 158 GPa, while the flexible portion may have a flexural modulus of about 1 GPa, about 5 GPa, about 9 GPa.

In some examples, the attachment mechanism may comprise a first clasp attached to the rigid proximal portion, a second clasp that interfits with the first clasp attached to the flexible distal portion, and a pull-wire slidably insertable within the first and second clasps. The attachment portion may have a first protracted configuration where the pull-wire secures the engagement between the first and second clasps and a second retracted configuration where the pull-wire releases the engagement between the first and second clasps. In another variation, the attachment portion may comprise a temperature-sensitive polymer segment (e.g., made from a thermoplastic material) that is attached and/or located between the rigid proximal portion and the flexible distal portion, where the temperature-sensitive polymer segment is configured to weaken when heated. In some examples, the attachment portion comprises a metal segment (e.g., an ionized metal segment) that may be attached between the rigid proximal portion and the flexible distal portion, where the metal segment may be configured to weaken when heated. In some variations, the attachment portion may comprise a metal segment susceptible to electrolytic dissolution that is attached between the rigid proximal portion and the flexible distal portion, where the metal segment is configured to dissolve when subjected to an electrical charge. In still other examples, the attachment portion may comprise a plug that is attached to the flexible distal portion, where the rigid proximal portion may comprise a lumen that is sized and shaped to frictionally retain the plug. In some examples, the attachment portion may comprise a screw joint, where the external thread of the screw joint is attached to the rigid proximal portion and the internal thread of the screw joint is attached to the flexible distal portion.

In some variations, the distal portion and the proximal portion are made from a same material and the proximal portion is stiffened by applying a stiffening agent. The guide element may be made of a material that is biodegradable or non-biodegradable. The distal portion of the guide element may have a length in the range of from about 5 cm to about 30 cm. The ratio of the axial length of the distal portion to the axial length of the proximal portion may be in the range of from about 0.05 to about 0.5. In some variations, the distal portion may comprise a monofilament and the proximal portion may be braided, while in other variations, the distal portion may be braided and the proximal portion may comprise a monofilament. In one variation, the proximal portion may comprise a larger outer diameter than the distal portion. The distal portion may be made from a first material, where the proximal portion may comprise at least one filament, and where the filament may be made from a second material that is stiffer than the first material. In some variations, the distal portion and the proximal portion may be coated with different materials.

Also disclosed herein is a tether-anchor assembly that may comprise a tether and a tissue-piercing anchor. The tether may comprise a rigid proximal portion and a flexible distal portion releasably attached the rigid proximal portion and the tissue-piercing anchor may comprise an eyelet, where the flexible distal portion of the tether may be coupled to the eyelet. In some variations, the anchor mat be fixedly coupled to said flexible distal portion of said tether via a knot assembly. The flexible portion may have a first torsional stiffness and the rigid portion may have a second torsional stiffness that is higher than the first torsional stiffness. The rigid portion may require a greater force prior to yielding in a compression test than the amount of force a flexible portion would require. In some variations, the proximal portion may comprise a first portion and a second portion, where the first portion is more rigid than the second portion. Alternatively or additionally, the rigid proximal portion may have a higher flexural modulus than the flexible distal portion (e.g., the rigid portion may have a flexural modulus of about 10 GPa, about 17 GPa, about 29 GPa, about 60 GPa, about 65 GPa, about 140 GPa, about 158 GPa, while the flexible portion may have a flexural modulus of about 1 GPa, about 5 GPa, about 9 GPa. In some variations, the proximal portion may comprise a first portion and a second portion, where the first portion may be more rigid than the second portion.

In one embodiment, a guide element is provided, where the guide element may comprise a distal portion having a first torsional stiffness, and a proximal portion having a higher torsional stiffness than the distal portion. The distal portion may be configured to be used as a tensioning element and may be detachable from the proximal portion. In further embodiments, the distal portion and the proximal portion may be made from a same material and the proximal portion may stiffened by the application of a stiffening agent. The material may be biodegradable or non-biodegradable. In some variations, the distal portion may be in the range of from about 5 cm to about 30 cm in length. In other variations, the ratio of the axial length of the distal portion to the axial length of the proximal portion is in the range of from about 0.05 to about 0.5. In one specific example, the distal portion may be a monofilament and the proximal portion may be braided. In another example, the distal portion may be braided and the proximal portion may be monofilament. In some other embodiments, the proximal portion may comprise a larger outer diameter than the distal portion. The change in diameter may be gradual or abrupt over 1 mm or more, sometimes in the range of about 2 mm to about 5 mm, and other times about 2 mm to about 4 mm. In another example, the distal portion may be made from a first material, wherein the proximal portion further comprises at least one filament, and wherein the filament may be made from a second material that is stiffer than the first material. In some other examples, the distal portion and the proximal portion may be coated with different materials.

In another embodiment, a tether is provided, where the tether may comprise a core element having a distal portion and a proximal portion, wherein the proximal portion is located in a tubular sheath, the sheath having a higher torsional stiffness than the core element. The distal portion may be configured to be used as a tensioning element and detachable from the proximal portion of the core element. The sheath may be made from a biodegradable material or a non-biodegradable material. The distal portion may have a length in the range of from about 5 cm to about 30 cm. In some further embodiments, the sheath may be slidably disposed along longitudinal axis of the core element.

In another embodiment, a tether may comprise a core element having a distal portion and a proximal portion, where the proximal portion may be coated with a material to increase the proximal torsional stiffness of the core element. The distal portion may be configured to be used as a tensioning element and may be detachable from the proximal portion of the core element.

In another embodiment, a device is provided, where the device may comprise a tubular polymeric tether having a distal portion and a proximal portion, and an inner core having a higher torsional stiffness than the tubular tether, where at least a portion of the inner core is located in the proximal portion of the tubular tether. The inner core may be made from a biodegradable material or a non-biodegradable material. In some examples, the inner core may be a guidewire. The distal portion of the tubular tether may have a length in the range of from about 5 cm to about 30 cm, and at least one portion of the tubular tether may be coated with one or more lubricious materials.

In still another embodiment, a tether-anchor assembly is provided, where the tether-anchor assembly may comprise a tether comprising a flexible distal portion and a stiff proximal portion, and an anchor comprising an eyelet region and a penetrating region configured to penetrate a tissue. The anchor may be fixedly coupled to the flexible distal portion of the tether via a knot assembly.

In another embodiment, a method of using a tether having a flexible distal portion and a rigid proximal portion is provided, where the method may comprise advancing the tether to a predetermined location, advancing a surgical device over the tether, detaching the distal portion from the proximal portion, and proximally withdrawing the proximal portion. In some variations, detaching the distal portion may comprise advancing a cutting device over the tether and cutting the distal portion from the proximal portion. The method may also further comprise positioning a plurality of anchors along said distal portion, and may further comprise attaching the plurality of anchors to cardiac tissue.

DETAILED DESCRIPTION

Figure 1:
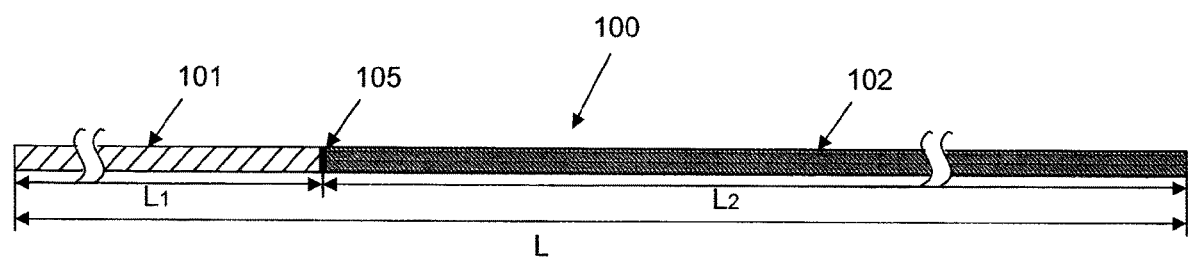
FIG. 1 is a side cross-sectional view of one embodiment of a tether with a flexible distal portion and a stiff proximal portion.

In many percutaneous or minimally invasive procedures, a guide element, such as a guidewire, may be used to facilitate insertion or passage of these instruments or implants to a remote body location, but in other procedures, a suture that is more flexible and serves as part of the implant may be also used. For example, the implantation of a surgical heart valve in an open heart surgery involves the placement of a plurality of separate sutures that are secured to tissue along the perimeter of the implantation site. Once all of the sutures are in place, the sutures are pulled taut and the heart valve is passed down the sutures to the implantation site. Each suture is then tied to secure the valve to the implantation site and the excess suture is removed. A suture, however, may be ill-suited for delivery of devices over longer, tortuous distances or with more rigid instruments, as the excessive flexibility of a suture may require excessive tensioning in order to resist displacement by the native anatomy or the rigid instruments passed over it.

Described herein are guide elements comprising tethers with a variable stiffness and methods of using the same. While exemplary methods of using these tethers in a mitral valve repair procedure are described in detail here, it should be understood from the outset that such devices and methods may be used, and are contemplated for use, in other medical procedures. Specific examples of devices and methods will now be described in further detail below.

Where tethers are used as guide elements, the tether may be permanently or temporarily secured. The implants may be any suitable implant, such as a tissue anchor or a pacemaker lead. In some embodiments, the implants may be advanced over the tether directly. In other embodiments, the implants may be deployed from one or more catheters that are advanced over the tether.

The use of tethers as guide elements may depend upon the distal end(s) of the guide element being secured in some fashion to the remote body location so that the distal end of the guide element may be pulled taut to facilitate passage of the heart valve. Furthermore, the actual effect of tether pulling on the ease of inserting an instrument or implant may vary based upon the remoteness and tortuosity of the insertion pathway. In contrast, a guidewire does not require tissue attachment, and is often configured or selected for a particular procedure to provide sufficient column strength to resist buckling when devices are inserted or withdrawn over the guidewire, in balance with sufficient flexibility to permit ease of passage along the insertion pathway to the remote body location.

In some examples, a tether may be one part of a cinchable implant system where other parts (e.g., tissue anchors) may be attached to tissues to tighten, compress or otherwise reconfigure the tissues. In one example, a procedure for reconfiguring annular tissue (e.g., mitral valve annular tissue and/or ventricular tissue at or near a heart valve) may comprise delivering a plurality of anchors into the tissue where the anchors are attached to a common tether. When multiple anchors are deployed to a region of the mitral valve annulus, the tether may be cinched or pulled proximally to tighten or compress the annular tissue. The result may be a geometric change in at least one of the mitral valve annulus and the tissue surrounding the mitral valve annulus, a reduction in the circumference of the mitral valve annulus, enhancement of mitral valve leaflet apposition, and/or a reduction in mitral valve regurgitation.

In some variations, the first anchor is fixedly attached or otherwise secured to the tether. After the first anchor is deployed and embedded into annular tissue and/or ventricular tissue at or near the mitral valve, the tether remains attached to the first anchor. One or more additional anchors may then be advanced over the tether into the patient and secured to other locations within the ventricle. Upon cinching the tether, the tether may be tied off or otherwise secured to maintain the tension and the unused proximal portion may then be cut and removed. The tether may then be used as a guide element for one or more catheters that are used to secure the tether, to cut and to remove the extra tether portion. The tensioned distal portion of the tether may be left at the target site to serve as a cinching implant itself.

In some variations, a tether may comprise one or more flexible portions and one or more stiff portions. FIG. 1 depicts an example of a tether 100 comprising a flexible distal portion 101 and a stiff proximal portion 102 with an overall length of L, while L1 is the axial length of the flexible distal portion 101 and L2 is the axial length of the stiffened proximal portion 102. The absolute and/or relative lengths of L1 and L2 may vary, and may be selected based upon in part on the particular procedure. In some embodiments, L1 may be in the range of about 5 cm to about 50 cm or greater, about 10 cm to about 40 cm, or about 20 cm to about 30 cm. In some embodiments, the ratio of L1:L2 may be in the range of about 0.01 to about 1, about 0.02 to about 0.8, or about 0.05 to about 0.5.

The mechanical properties of the flexible and stiff or rigid portions may be characterized by their torsional stiffnesses. Torsional stiffness is a measure of the resistance offered by an elastic body to certain deformations (e.g., bending, kinking or buckling). K1 is the torsional stiffness of the distal tether portion 101 and K2 is the torsional stiffness of the proximal tether portion 102. In some embodiments, the ratio of K1:K2 may be in the range of about 0.01 to about 0.5, about 0.02 to about 0.3, or about 0.05 to about 0.1. In some embodiments, a tether with variable stiffness may be a composite tether comprising sections with different torsional stiffness. The torsional stiffness of a tether may be a function of several variables including the tether material, tether coating, tether size and structural configuration. Any one of or any combination of these variables may be changed to construct different sections of one tether independently.

Alternatively or additionally, the mechanical properties of the flexible and stiff or rigid portions may be characterized by their bending stiffness. Bending stiffness reflects the amount of force required to cause an elastic body to bend and/or deflect. For example, the bending stiffness of an elongate body such as a wire, tube (e.g., hypotube), or tether may be characterized by applying a force perpendicular to the longitudinal axis of the elongate body and determining the magnitude of the force required to cause the elongate body to bend or yield. A rigid elongate body may have a higher bending stiffness than a flexible elongate body (i.e., the magnitude of the force applied perpendicularly to rigid elongate body that causes it to initially bend is greater than the force needed to cause a flexible elongate body to initially bend). For example, a rigid elongate body may have a flexural rigidity of about 50 N(mm$^2$) to about 600 N(mm$^2$), e.g., about 50 N(mm$^2$) to about 150 N(mm$^2$), about 150 N(mm$^2$) to about 300 N(mm$^2$), about 300 N(mm$^2$) to about 400 N(mm$^2$), 400 N(mm$^2$) to about 500 N(mm$^2$), 500 N(mm$^2$) to about 600 N(mm$^2$), about 50 N(mm$^2$), about 60 N(mm$^2$), about 75 N(mm$^2$), about 150 N(mm$^2$), about 200 N(mm$^2$), about 225 N(mm$^2$), about 275 N(mm$^2$), about 325 N(mm$^2$), about 375 N(mm$^2$), about 425 N(mm$^2$), about 475 N(mm$^2$), about 500 N(mm$^2$), about 525 N(mm$^2$), about 575 N(mm$^2$), about 600 N(mm$^2$), while a flexible elongate body with a low bending stiffness may have a flexural rigidity that is less than 50 N(mm$^2$), e.g., about 0.1 N(mm$^2$) to about 1.5 N(mm$^2$), about 1.5 N(mm$^2$) to about 3 N(mm$^2$), about 3 N(mm$^2$) to about 10 N(mm$^2$), about 10 N(mm$^2$) to about 20 N(mm$^2$), about 20 N(mm$^2$) to about 30 N(mm$^2$), about 30 N(mm$^2$) to about 40 N(mm$^2$), about 40 N(mm$^2$) to about 50 N(mm$^2$), about 0.25 N(mm$^2$), about 0.5 N(mm$^2$), about 1.0 N(mm$^2$), about 1.5 N(mm$^2$), about 5 N(mm$^2$), about 10 N(mm$^2$), about 20 N(mm$^2$), about 30 N(mm$^2$), about 40 N(mm$^2$), about 45 N(mm$^2$), about 48 N(mm$^2$), about 49 N(mm$^2$). Alternatively or additionally, the mechanical properties of the flexible and stiff or rigid portions may be characterized by their column strength. The column strength of an elongate body such as a wire, tube, or tether may be characterized by applying a force coaxial with the longitudinal axis of the elongate body and determining the magnitude of the force required to cause the elongate body to bend or yield. Column strength may also be characterized by the axial compressive load that may be sustained by an elongate body before yielding to the load (e.g., such as during compression testing). In some variations, a rigid elongate body may have a higher column strength than a flexible elongate body (i.e., the magnitude of the axial force required to cause a rigid elongate body to bend is greater than the axial force needed to cause a flexible elongate body to bend). A rigid elongate body with a higher column strength than a flexible elongate body may have a hardness value between about 10 Vickers to about 500 Vickers, e.g., about 10 Vickers to about 20 Vickers, 20 Vickers to about 35 Vickers, 35 Vickers to about 50 Vickers, about 50 Vickers to about 75 Vickers, 75 Vickers to about 150 Vickers, 150 Vickers to about 300 Vickers, 300 Vickers to about 450 Vickers, 450 Vickers to about 500 Vickers, about 10 Vickers, about 15 Vickers, about 20 Vickers, about 35 Vickers, about 50 Vickers, about 75 Vickers, about 100 Vickers, about 150 Vickers, about 200 Vickers, about 225 Vickers, about 275 Vickers, about 325 Vickers, about 375 Vickers, about 425 Vickers, about 475 Vickers, about 485 Vickers, about 500 Vickers. Alternatively or additionally, the mechanical properties of flexible and stiff or rigid portions may be characterized by their flexural modulus. For example, under a three-point bending test using a tensile testing machine, a stiff or rigid elongate body may have a flexural modulus from about 5 GPa to about 400 GPa, e.g., about 5 GPa to about 20 GPa, about 20 GPa to about 35 GPa, about 35 GPa to about 75 GPa, 75 GPa to about 150 GPa, about 150 GPa to about 250 GPa, about 250 GPa to about 350 GPa, about 350 GPa to about 400 GPa, about 5 GPa, about 10 GPa, about 15 GPa, about 17 GPa, about 25 GPa, about 29 GPa, about 60 GPa, about 65 GPa, about 140 GPa, about 158 GPa, about 180 GPa, about 200 GPa, about 225 GPa, about 250 GPa, about 275 GPa, about 300 GPa, about 325 GPa, about 375 GPa, about 385 GPa, etc. A flexible elongate body may have negligible or minimal flexural modulus, and may be deformable and deflectable under the forces of its own weight. In some variations, a tether with a proximal portion that has a high column strength may be able to push a distal portion of the tether despite the tortuosity of the tether path (e.g., the proximal rigid portion may be considered "pushable" while the distal flexible portion may not be considered "pushable", since it may deform and/or deflect under the pressure of its own weight).

The configuration, cross-sectional shape and/or size of the distal portion 101 and the proximal portion 102 may be the same or may be different. The cross-sectional shape may be circular, ovoid, rectangular, triangular, polygonal, or ribbon-like, for example. The tether may have a monofilament or multi-filament configuration, which may be twisted, braided or woven. In some variations, to facilitate passage and withdrawal of instruments or implants using the tether 100, the diameters of the flexible distal portion 101 and the stiff proximal portion 102 may be configured to be generally similar. In other variations, the diameters of the flexible distal portion 101 and the stiff proximal portion 102 may be configured to be different. In the latter variations, the tether 100 may comprise a taper section to facilitate transition between the flexible distal portion 101 and the stiff proximal portion 102. The taper section may be generally located along the attachment region between the flexible distal portion and the stiff proximal portion, along the flexible distal portion, along the stiff proximal portion, or a combination thereof.

Figure 2A:
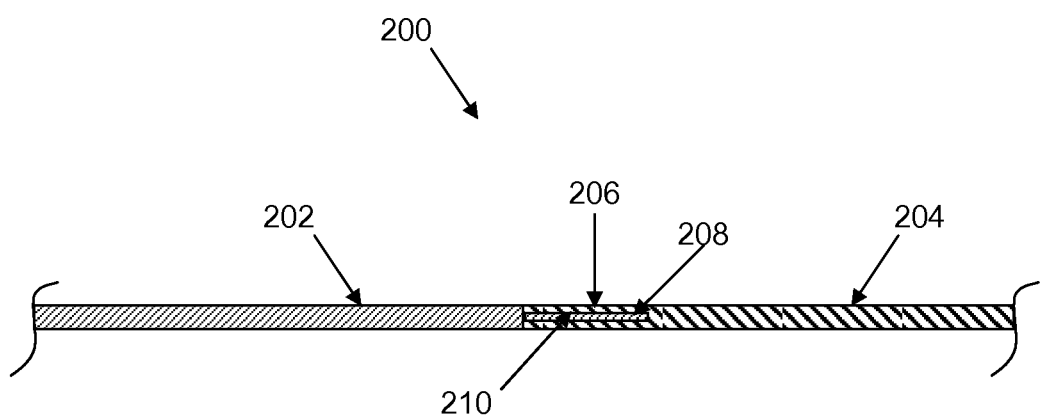
FIGS. 2A and 2B are schematic representations of other embodiments of a variable stiffness tether-guidewire.

Referring to FIG. 2A, in some variations, the tether 200 may be a tether-guidewire comprising a flexible distal portion 202 and a stiff guidewire-based proximal portion 204. The flexible distal portion 202 may comprise synthetic or natural materials, may be monofilament or multi-filament, and may be resorbable or non-resorbable. The guidewire structure may comprise any of a variety of guidewire configurations, while further comprising a distal guidewire section 206 with an interior lumen 208 or cavity configured to attach to a proximal section 210 of the flexible distal portion 202. For example, the stiff proximal portion 204 may generally comprise a guidewire structure with a smaller wire helically wound around a larger core wire, but wherein the distal guidewire section 206 lacks a core and instead the smaller wire may be crimped and/or helically wound around the proximal end 210 of the flexible distal portion 202. The interface between the interior lumen 208 and the proximal section 210 may be an interference or friction fit, but in some examples may also be glued together. In variations where the polymeric material used for the flexible distal portion 202 comprises a compressible material and/or configuration, the proximal section 210 of the flexible distal portion 202 may comprise a compressed state of the otherwise same material and structure. In other variations, the proximal section 210 of the flexible distal portion 202 may be configured differently than the rest of the flexible distal portion 202. For example, the polymeric material or the filaments comprising it may be tapered or otherwise have a reduced diameter or cross-sectional dimension, which may be more easily inserted or otherwise attached to the interior lumen 208 of the stiff proximal portion 204 during the manufacturing process.

Figure 2B:
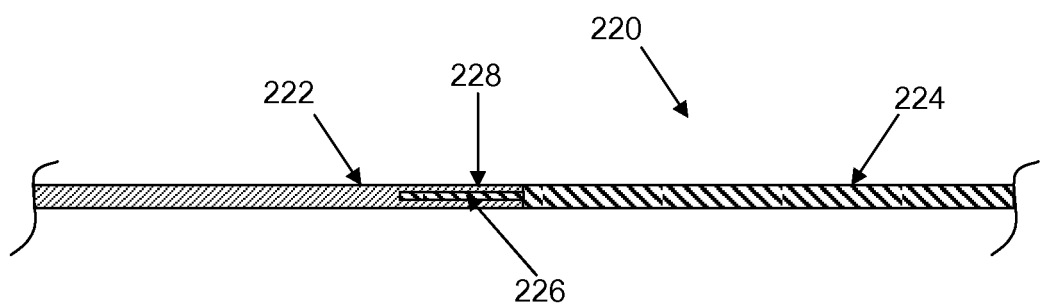

In another variation depicted in FIG. 2B, the tether 220 comprises a distal portion 222 and a guidewire-based proximal portion 224, wherein the proximal portion 224 comprises a reduced size distal section 226 over which a tubular proximal section 228 of the distal portion 222 is attached. In some variations, the tubular proximal section 228 is secured to the reduced size distal portion 226 using adhesives, while in other examples, tubular proximal section 228 may be tightly woven over the reduced size distal section 226 and secured by an interference fit. In still other variations, the reduced size distal section 226 of the proximal portion 224 may comprise ridges, slots, or lumens into which the filaments (if any) of the distal portion 222 may sit in or pass through. Of course, a combination of securing modalities may also be used. In some further variations, the reduced size distal section 226 may comprise ridges and/or recesses to further facilitate a mechanical or resistance interfit between the tubular proximal section 228 and the reduced size distal section 226.

In some embodiments, the tether may have a diameter in the range of from about 0.01 mm to about 0.8 mm sometimes about 0.03 mm to about 0.5 mm, and other times about 0.1 mm to about 0.25 mm. The flexible distal portion of the tether may comprise any of a variety of materials. In some variations, the tether may be formed of a biodegradable material, which may be configured to degrade over a period of days, weeks, months, or even years. Examples of suitable biodegradable materials include, but are not limited to, polyglactin (e.g., VICRYL, POLYGLACTIN 910), polydioxanone (e.g., PDS), polyglecaprone 25 (e.g., MONOCRYL), polyglyconate (e.g., MAXON), polyglycolic acid (e.g., DEXON), polylactic acid, and processed collagen (e.g., catgut). In other variations, the tether, or a portion thereof, may also be formed of one or more non-biodegradable materials. Examples of non-biodegradable materials include, but are not limited to, polyester (e.g., DACRON, ETHIBOND, ETHIFLEX, MERSELINE, TICRON), polypropylene (e.g., PROLENE, SURGILENE), nylon (e.g., ETHILON, DERMALON), polytetrafluoroethylene, silk, linen, and GORE-TEX. In still other variations, the tether may be formed of a combination of one or more biodegradable materials and one or more non-biodegradable materials.

The stiff proximal portion may comprise the same material as the flexible proximal portion, and/or may comprise a relatively stiffer material. Examples of stiffer materials include, but are not limited to metals (absorbable or non-absorbable), metal alloys (e.g., stainless steel, a nickel-titanium alloy, etc.), and polymer materials with relative high stiffness (e.g. polyethylene terephthalate (PET), poly (vinyl alcohol) (PVA), poly(vinyl chloride) (PVC), polystyrene, poly(methylmethacrylate), poly(carbonate), or any combination thereof).

In other embodiments, the distal portion and the proximal portion of a tether may be made from the same material, including a single contiguous material, but they may be coated with different coating materials. In yet other embodiments, the distal portion and the proximal portion may comprise different structural configurations. In some variations, for example, the distal portion may be braided and the proximal portion may be monofilament, but in other variations, the distal portion may be monofilament and the proximal portion may be braided. In still other embodiments, the distal portion may have a smaller outer diameter than the proximal portion. It should be understood that while embodiments of tethers comprising one flexible distal portion and one stiff proximal portion are described in detail here, embodiments of tethers with variable stiffness may comprise more than one flexible portion and more than one stiff portion.

In some embodiments, the tether may be coated with one or more lubricious materials to reduce abrasion and/or friction during advancement or withdrawal of any devices over the tether. In further embodiments, where the distal tether portion is knotted or otherwise secured to an implant, a lubricious coating on the surface of the tether may promote knot tie-down performance (i.e. the ease of tying a knot onto the implant). Some variations of lubricious coating materials may be hydrophilic, while other variations of lubricious coating materials may be hydrophobic. For example, a hydrophobic polymer, such as a polyxylene polymer (e.g., parylene) may be used. Additional examples of suitable lubricious coating materials include polytetrafluoroethylene (PTFE, e.g., TEFLON, HOSTAFLON) and other suitable materials known to those skilled in the art.

In other variations, the tether may be coated with at least one coating material to alter one or more other characteristics of the tether, including but not limited to biocompatibility, anti-infective properties and/or abrasion resistance. Non-limiting examples of such coatings include biocompatible wax, silicone (e.g., Dow Corning silicone fluid 202A), silicone rubbers (e.g., Nusil Med 2245, Nusil Med 2174 with a bonding catalyst), PBA (polybutylate acid), ethyl cellulose (Filodel), silver, fibrin glue, polymethylmethacrylate (PMMA) cement, hydroxyapatite cement, antibiotic spray, collagens, liposomes, collagen scaffold, polylactic acid, polyhydroxyethyl methacrylate (pHEMA), polyvinylalcohol and gum arabica blend matrix, and combination thereof. A single coating material may be used, or combinations of coating materials may be used.

In some variations, a tether may include one or more therapeutic agents. In some embodiments, the tether may comprise one or more lumens and/or cavities from which one or more therapeutic agents may be delivered. The tether may be partially or entirely coated or impregnated with one or more therapeutic agents, and may further comprise a carrier material or an elution-control material. In other embodiments, the carrier material or an elution-control material may be a biodegradable material that is mixed with the therapeutic agent(s). In other embodiments, the carrier or elution-control material may comprise a degradable microstructure, such as a sphere or cavity, that encapsulates one or more of the therapeutic agents. Non-limiting examples of therapeutic agents include Vascular Endothelial Growth Factor (VegF), Fibroblast Growth Factor (FGF), Platelet-Derived Growth Factor (PDGF), Transforming Growth Factor Beta (TGFbeta, or analogs), insulin, insulin-like growth factors, estrogens, heparin, and/or Granulocyte Colony-Stimulating Factor (G-CSF).

Figure 3:
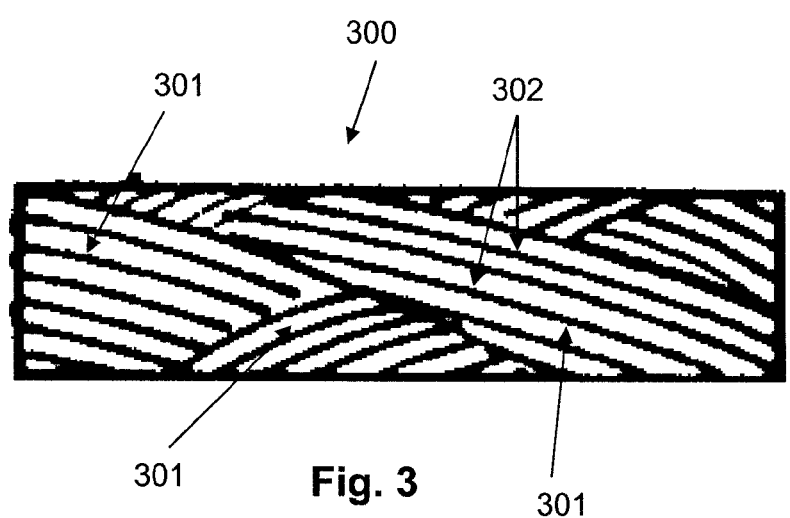
FIG. 3 is a partial perspective view of a multifilament tether comprising a reinforcing material.

In some variations, the proximal tether portion may be reinforced with one or more reinforcement materials or structures. In some embodiments, one or more reinforcing materials may be co-extruded with one or more materials from which the tether is originally made. In some embodiments where the tether is braided, at least one filament in the proximal tether portion may comprise a reinforcement material. In some variations, more than one filament may comprise combinations of reinforcement materials. As illustrated in FIG. 3, in some embodiments where a tether 300 comprises multi-filament strands 301 (i.e., each strand 301 may comprise multiple filaments 302), at least one filament 302 in one or more strands 301 of the proximal tether portion may comprise one or more reinforcing materials. In some variations, more than one filament 302 in one or more strands 301 of the proximal tether portion may comprise combinations of reinforcing materials. Reinforcement materials may be any kind of materials that may increase the column strength of the proximal tether portion. Examples of such reinforcing materials may include, but are not limited to metals (absorbable or non-absorbable), metal alloys (e.g., stainless steel, a shape memory nickel titanium alloy, etc.), polymer materials with relative high stiffness (e.g., polyethylene terephthalate (PET), poly(vinyl alcohol) (PVA), poly (vinyl chloride) (PVC), Polystyrene, Poly(methylmethacrylate), Poly(carbonate), or any combination thereof.), or other suitable biocompatible materials.

Figure 4A:
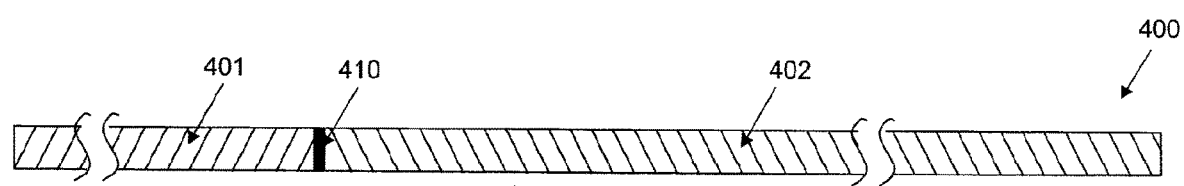
FIGS. 4A to 4D illustrate different embodiments of interface between a flexible distal tether portion and a stiff proximal tether portion.
Figure 4B:
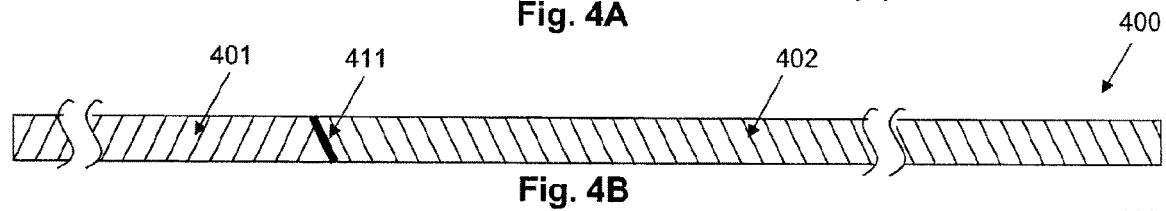
Figure 4C:
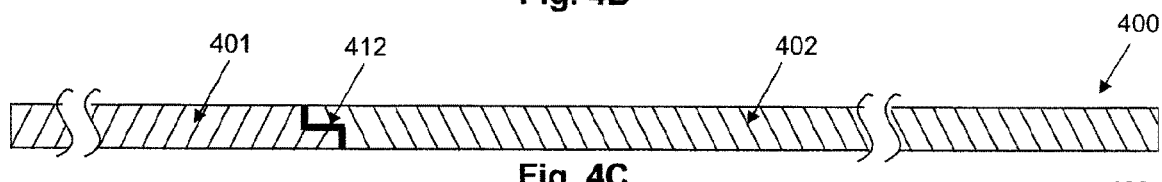
Figure 4D:
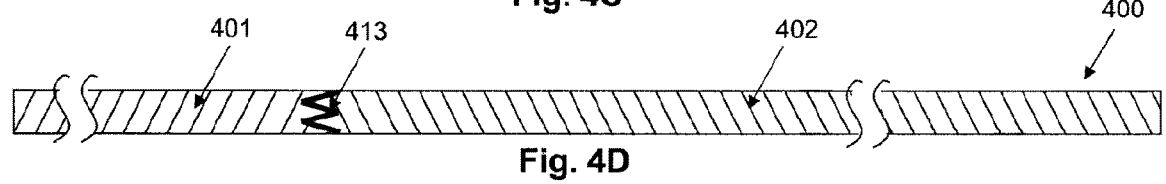

In some embodiments, different portions of the tether may be connected by adhesive, fusing, brazing and/or soldering or any other suitable techniques known to those skilled in the art. Different portions of the tether may be connected by one or more magnets (e.g., rare earth magnets, electromagnets, magnetic materials, and the like). In other embodiments, portion of the tether with different characteristics may be integrally formed using a co-extrusion process. FIGS. 4A to 4D illustrate some embodiments of the interface between one flexible distal portion 401 and one stiff proximal portion 402 of a tether 400. In some embodiments, the interface may have a relative linear configuration 410, 411 as depicted in FIGS. 4A and 4B. In some embodiments, the linear interface 411 may comprise a slope in order to have a larger contacting surface between the distal portion 401 and the proximal portion 402. In other embodiments, the interface may comprise a non-linear configuration. For example, the interface may comprise a step pattern 412 as illustrated in FIG. 4C. In yet another embodiment, the interface may comprise a zig-zag pattern 413, as illustrated in FIG. 4D.

Figure 5A:
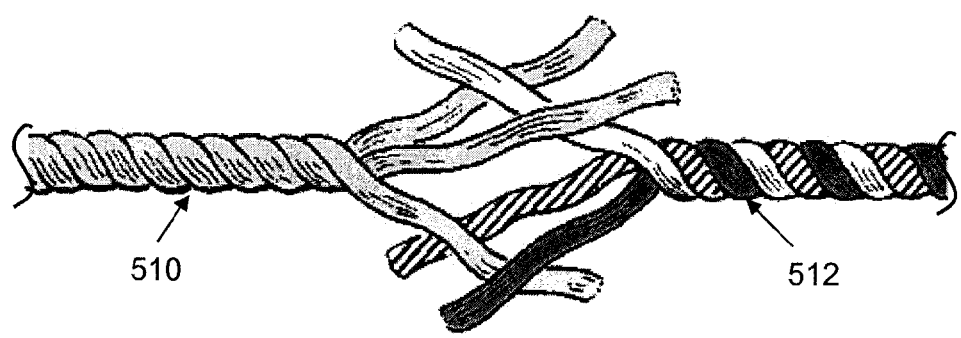
FIGS. 5A to 5C illustrate one embodiment of a method of connecting two multifilament tethers using a short splice.
Figure 5B:
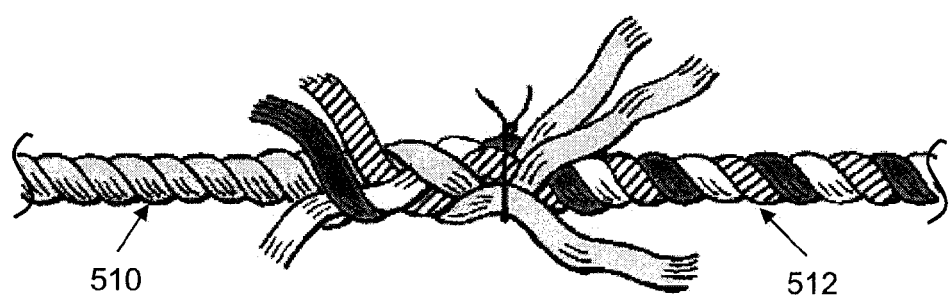
Figure 5C:

In some embodiments where both the distal portion and the proximal portion of a tether are braided, these two portions may be connected by a splice. FIGS. 5A to 5C are schematic illustrations of a method of connecting two three-filament tethers 510 and 512 with a short splice. In other embodiments, braided tethers 510 and 512 may comprise four filaments, five filaments, ten filaments, and the like. In other embodiments, other type of splice, for example a long splice may be used to connect the two braided tether portions.

In some variations, the tether may generally comprise a polymeric material or polymeric structure along a substantial portion of its length, but where the stiffness of the proximal tether portion may result from being coated or infused with one or more stiffening materials. Examples of such stiffening coating materials include, but are not limited to homopolymers and copolymers of epoxies, vinyl alcohols, hydroxy alkyl methacrylates, acrylamides, n-vinyl pyrrolidones, alkylene oxides, cyanoacrylates, low melting polylactone polymers and copolymers, waxes, shellacs, carboxyalkyl celluloses, alginic acid, poly-n-acetyl glucose amines, gelatins and mixtures and copolymers thereof. The stiffening coating materials may be applied onto the proximal tether portion in any number of ways. For example, the proximal tether portion may be submerged in a stiffening coating material, or solution thereof until a desired degree of torsional stiffness is acquired. Excess stiffening coating material can be removed by drainage, wiping, blowing or evaporation. In other variations, the stiffening coating material may be applied by spraying, brushing or any other suitable techniques known to those skilled in the art. In some variations, a single coating of stiffening material may be applied. In other variations, multiple stiffening coating materials may be applied.

Referring back to FIG. 1, in some variations, the flexible distal tether portion 101 may be separated from the stiff proximal tether portion 102. After the use of the distal tether portion 101 is completed, a separation device can be passed down the proximal tether portion 102 to cut off or otherwise separate the distal portion 101. One example of such detaching device is disclosed in more detail in U.S. application Ser. No. 12/253,885, entitled "Devices and Methods for Termination", which is hereby incorporated by reference in its entirety. In some embodiments, the distal tether portion 101 may comprise one or more radiopaque materials (e.g., a metal such as gold or aluminum), or other contrast-enhancing agents. The radiographic markers may be used by the healthcare provider to identify the location of the proximal end 105 of the distal tether portion 101 and hence be able to separate this portion.

Figure 6:
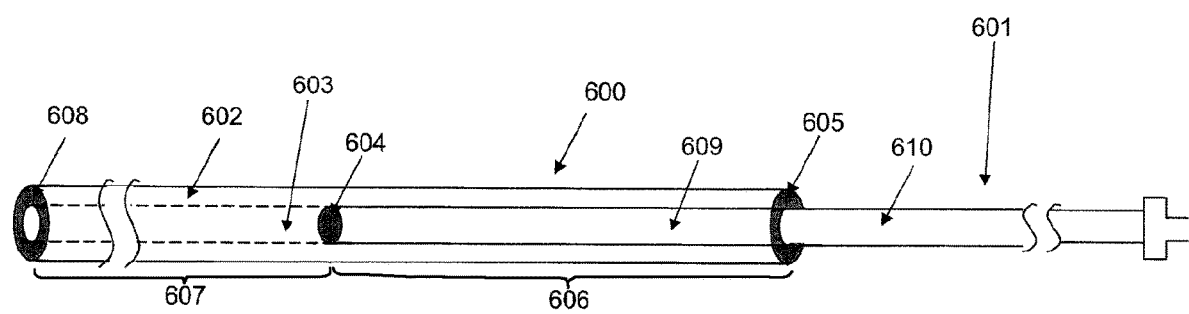
FIG. 6 is schematic perspective view of a guidewire removably located in a tubular tether.

FIG. 6 illustrates another variation of a tether 600 with variable stiffness. The tether 600 comprises a flexible tubular tether element 602 comprises a lumen 603 with a guidewire or other support element 601 partially located in lumen 603. The distal portion 607 of the tether 600 is more flexible and may be easily cinched, tightened and/or severed, while the proximal portion 606 is more a torqueable and kink-resistant as a result of the support element 601. Although the lumen 603 is depicted in FIG. 6 along the entire length of the tubular tether element 602, between is proximal end 605 and distal end 608, in other variations, the portion of the lumen 603 that is distal to the distal end 604 of the support element 601 may be collapsed (e.g. heat shrunk) or comprise a flexible and/or compressible material (e.g. another filament, gel, etc.). In some variations, the support element 601 may be attached to the tubular tether element 602 along its entire length or at one or more locations by any suitable technique, including but not limited to gluing, fusing, brazing and/or soldering, magnetic components, or the like. In some embodiments, the distal end 604 of support element 601 may comprise one or more radiopaque materials or other contrast-enhancing agents that may facilitate confirmation of the tether, including but not limited to identifying to location along the distal portion 607 where the tether 600 will be cut or separated. The distal end 604 of the support element 601 may be squared off or tapered.

In other variations, the support element 601 may not be specifically attached to the tubular tether elements 602 but a friction fit between the support element 601 and the tubular tether structure 602 may resist relative movement between the two. In these variations, once the distal portion 607 of the tether 600 is secured to the target location (either directly or indirectly via a tissue anchor or other implantable structure attached to the target location), the support element 601 may be pulled and/or removed.

In some embodiments where the tether with variable stiffness described herein will be used as a cinchable implant to cinch implant members and tighten tissues, at least one implant member (e.g. an anchor) may be coupled to the flexible distal portion of the tether through a knot. Non-limiting examples of suitable knot configurations include bowline knots, figure-of-eight knots, splices (e.g., cut splices, horseshoe splices, long splices, short splices, side splices, eye splices, back splices, etc.) and the like. Examples of such tether-anchor assemblies are disclosed in more detail in U.S. patent application Ser. No. 12/505,332, filed Jul. 17, 2009, entitled, "Tether-Anchor Assemblies", which is hereby incorporated by reference in its entirety.

Figure 7A:
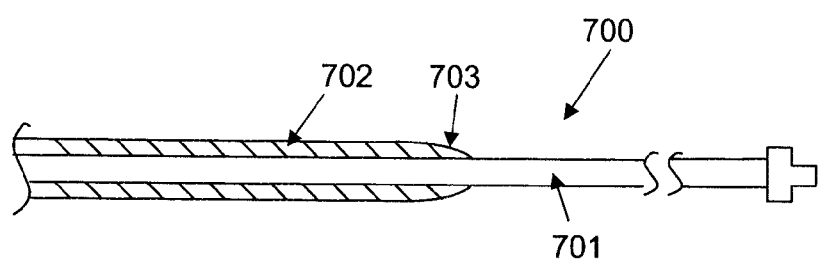
FIGS. 7A and 7B are partial cutaway side views of different embodiments of interface between a tubular tether and a guidewire removably located in the tubular tether.
Figure 7B:
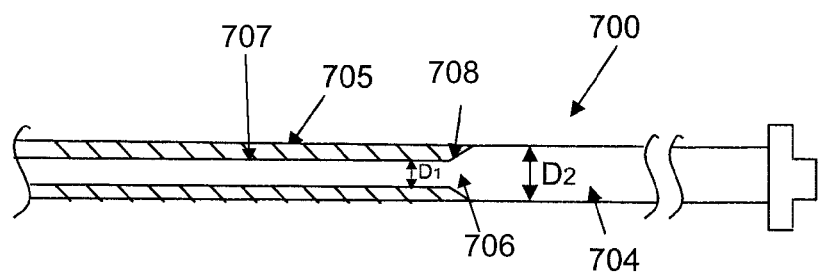

In some embodiments, the entire axial length of the guidewire or support element may be covered by the tubular tether element. In other embodiments, as illustrated in FIG. 6, only a distal portion 609 of support element 601 is covered, while a proximal portion 610 remains bare. In some embodiments, the tubular tether element may be configured such that there is a smooth transition between the surface of the bare support element and the proximal end of the tubular tether element. In FIG. 7a, for example, the tether 700 comprises a tubular tether element 702 with a proximal end 703 comprising a tapered configuration, which provides a gradual change in diameter to the smaller diameter support element or guidewire 701. In other variations as illustrated in FIG. 7B, a guidewire 704 and the tubular tether element 705 may comprise a uniform diameter by configuring the outer diameter of guidewire 704 with a tapered section 706 that decreases from D2 to D1. Likewise, the lumen 707 of the tubular tether element 705 may comprise a corresponding taper section 708 that is configured to accept the tapered section 706 of the guidewire 704. Together, the overall tether device 700 may comprise substantially the same outer diameter along its longitudinal axis.

Referring back to FIG. 6, in variations comprising a tether 600 with a distal portion 607 where the lumen 603 remains intact (e.g. not filled or glued shut), when the distal portion 607 is compressed or pulled taut, the lumen 603 may collapse into a reduced or flattened annular cross section. In these variations, the flattened tether portion may comprise a larger contact surface with tissues than a traditional tether with a round cross section, which may reduce the likelihood of impinging, tearing or cutting of the tissue. Moreover, if such flattened tether portion is used to couple the tether to an implant by a knot, the flattened configuration may improve the security of the tie knot also because of the larger contact surface area. In some variations, the hollow portion at the distal end of the tether may be used to store or deliver one or more therapeutic agents. The therapeutic agents may be used, for example, to treat the target site to which the tether is fixedly attached or otherwise secured. In some variations, the therapeutic agents may be squeezed out or extrude from the distal end 608 of the distal portion 607, but in other examples, the distal portion 607 may comprise perforations (e.g. formed during manufacturing or as a result of a multi-filament braid or weave configuration), such that the therapeutic agents may be released through the walls of the distal portion 607.

In some embodiments where the guidewire is not attached to the tubular tether, the axial length of the flexible tether portion may be varied at some point during a medical procedure. The operator may proximally push or pull the guidewire using enough forces to overcome the frictional resistance between the guidewire and the tether. In some embodiments, the radiopaque materials or other contrast-enhancing agents may be embedded at the distal end of the guidewire and inform the operator the location of the guidewire.

In some embodiments, the guidewire may be any type of stiffening inner core with a higher torsional stiffness than the outer tether portion. The inner core may comprise a linear configuration, a non-linear configuration, or a combination thereof. The inner core can be made of metal (e.g., copper, silver, aluminum, etc.) or metal alloy (e.g., nickel-titanium alloy, spring stainless steel, etc.). The inner core can also be made of non-metal materials. The inner core can be a monofilament or multifilament assembly. At least a portion of the inner core may be coated with one or more lubricious materials. Non-limiting examples of such lubricious coating materials are listed in previous sections.

Figure 8A:
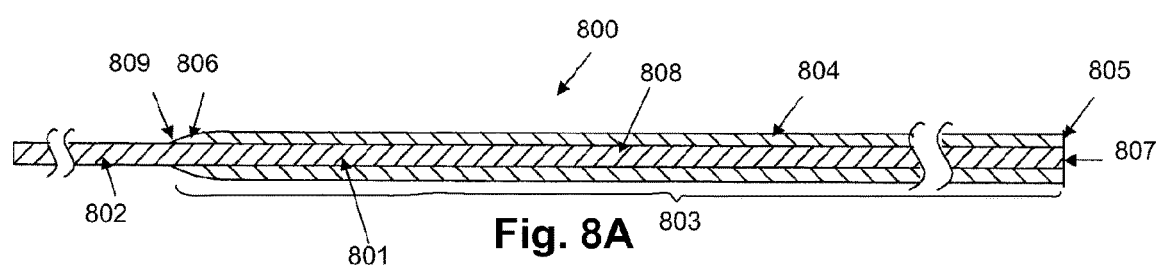
FIG. 8A is a side cross-sectional view of one embodiment of a tether with a stiffening sheath.
Figure 8B:
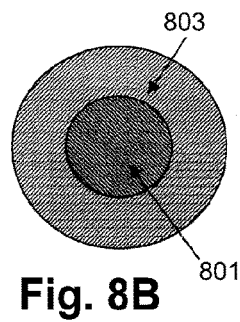
FIG. 8B is a superior cross-sectional view of the embodiment from FIG. 8A.

In some embodiments, the tether may be configured with a flexible core with a proximal tether portion may be stiffened by a stiffening sheath placed over proximal tether portion. FIG. 8A, for example, is a longitudinal cross-sectional view of a tether 800 comprising a flexible core 801 with an exposed distal section 802 and a proximal portion 803 located within a stiffening sheath 804. FIG. 8B is an axial cross-sectional view through the proximal portion 803 of the embodiment from FIG. 8A. In some embodiments, sheath 804 may be co-extruded with flexible core 801. In some embodiments, sheath 804 may be attached to the flexible core 801 at one or more locations along the axial length of flexible core 801. Sheath 804 may be attached to flexible core 801 by crimping, gluing, fusing, brazing and/or soldering, magnetic components, or any suitable techniques known to those skilled in the art. In still other embodiments, a friction fit is provided between tether 800 and sheath 803 that may resist relative movement between the two components. In some variations, the friction fit may be configured to permit withdrawal of the sheath 804 from the tether 800 with the use of sufficient force.

Figure 8C:
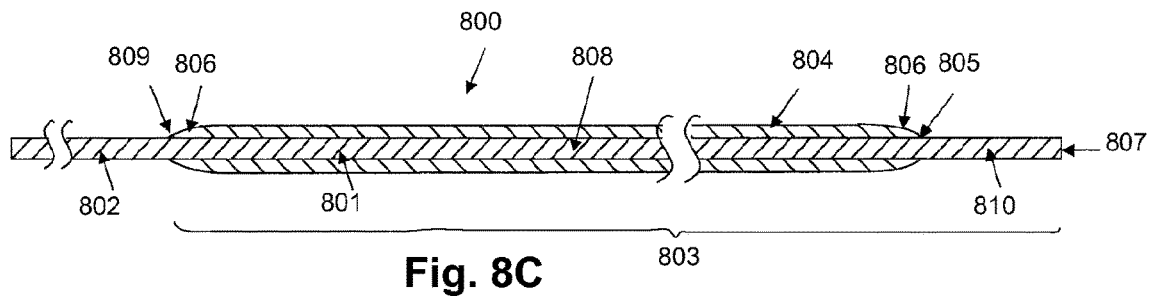
FIG. 8C is a side cross-sectional view of another embodiment of a tether with a stiffening sheath.

In some embodiments, sheath 804 may cover the entire proximal portion 803 of flexible core 801, as illustrated in FIG. 8A. In other embodiments, depicted in FIG. 8C, sheath 804 only covers a middle portion 808 of flexible core 801, leaving a distal end portion 802 and a proximal end portion 810 of the flexible core 801 uncovered. In some embodiments, the interface of the sheath 804 and the flexible core 801 is configured such that there is a smooth transition between the surface of the sheath and the surface of the tether. In FIG. 8A, for example, a tapered transition region 806 is provided at the distal end 809 of the sheath 804, while no transition region is provided at the proximal end 805. In FIG. 8C, sheath 804 may comprise tapered transition regions 806 on both the proximal end 805 and distal end 809. The tapered transition regions 806 may be configured so that the advancement and/or withdrawal of an implant or a catheter over the interface between sheath 804 and flexible core 801 will not be disrupted by an abrupt outer diameter change of tether 800.

In some examples, a stiffening sheath may comprise a type of elongated tubular structure with greater torsional stiffness than the proximal tether portion. In some examples, the stiffening sheath may be a tubular wire or a braided mesh. The stiffening sheath may be made from a metal (absorbable or non-absorbable), a metal alloy (e.g., stainless steel, a shape memory nickel titanium alloy, etc.), a non-metal material (e.g., a polymeric material coated with one or more stiffened coating materials), or any other biocompatible material(s). In some embodiments, the inner surface, the outer surface or both surfaces of a stiffening sheath may be coated with one or more lubricious coating materials described above to enhance axial passage of instruments over the sheath. In some variations, surfaces of the stiffening sheath may be coated with other coating materials to improve its biocompatibility, anti-infective properties, abrasion resistance and/or other desirable characteristics.

As illustrated in FIG. 8A, in some embodiments where sheath 804 is not fixedly attached to flexible core 801, sheath 804 may be manipulated to vary the length of the distal portion 802. In some variations, the tether 800 may be configured to permit both pushing and pulling of the sheath 804, while in other variations, the sheath may only be pulled. The configurational change may be performed by manipulating the proximal end 805 of the sheath 804 relative to the proximal end 807 of the support element or guidewire 801. In some variations, the entire sheath 804 may be proximally withdrawn from the flexible core 801.

Figure 10A:
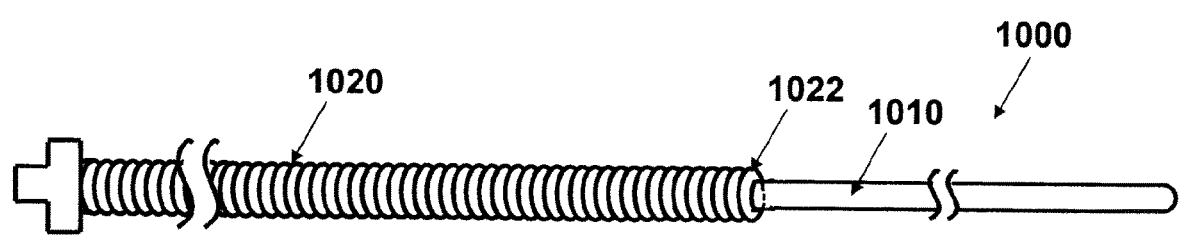
FIGS. 10A and 10B schematically illustrate tether-guidewire devices having a coiled spring and twisted-braid guidewire configurations, respectively.
Figure 10B:
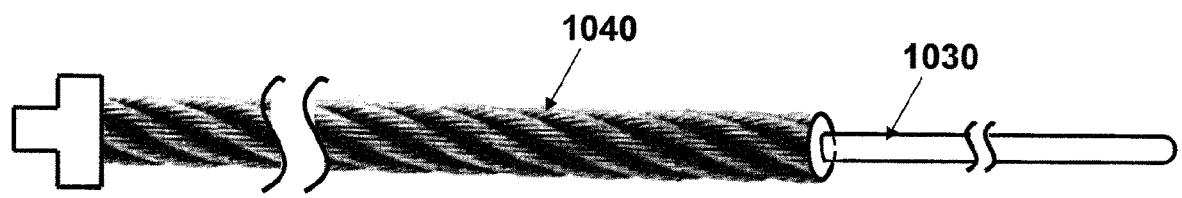

In some embodiments, a tether-wire assembly may be formed by coupling the proximal end of a tether with the distal end of a wire. FIG. 10A illustrates one embodiment of a tether-wire assembly 1000 comprising a tether 1010 distally coupled to a guidewire 1020 having a coiled spring configuration. The proximal portion of the tether 1010 may be attached by the tight coiling of the guidewire 1020 to form a resistance interfit, and/or the distal end 1022 of the wire 1020 may be crimped to secure the tether 1010. Alternatively, the wire 1020 and the tether 1010 may be crimped together with a crimping member, a crimping ring or sleeve, for example, or woven into the coils of the guidewire. In other embodiments, the tether may be coupled to the guidewire by gluing, melting, soldering, magnetic components, or any other suitable techniques known to the ordinary skilled in the art. FIG. 10B schematically illustrates another embodiment of a tether-wire assembly comprising a twist-braided guidewire 1040 with a tether 1030 distally attached thereto. The tether 1030 may be crimped between filaments of the wire 1040 in order to be attached to the distal end of the wire 1040. In other embodiments, the twisted configuration of the guidewire may be tightly twisted around or with the tether to form a resistance interfit. The distal end of the braided guidewire may be crimped, melted or otherwise closed to resist fraying. In still other embodiments, if the tether 1030 is braided, the tether 1030 may be attached to the wire 1040 with a splice. In still other embodiments, the tether 1030 may be glued or welded to the distal end of the braided wire 1040. The coiled spring guidewire 1020 and the twist-braided guidewire 1040 are only two exemplary embodiments of a wire that may be used to form a tether-wire assembly, wires with other configurations, for example, a solid wire, may be used as well.

Figure 11A:
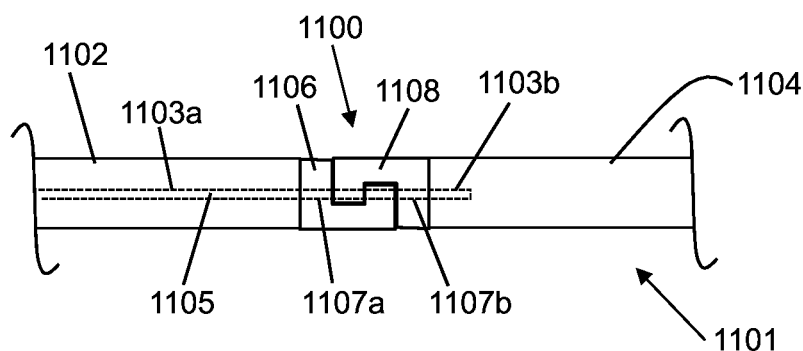
FIGS. 11A to 11D depict different variations of attachment mechanisms that may be used to attach a flexible distal tether portion and a stiff proximal tether portion.

In some embodiments, the different portions of a variable stiffness guide element or tether may be releasably attached by various attachment mechanisms other than the previously described attachment mechanisms. Additional variations of releasable attachment mechanisms that may be used with a variable stiffness tether are depicted in FIGS. 11A to 11D. One variation of an attachment mechanism 1100 between a proximal rigid portion 1102 and a distal flexible portion 1104 of a variable stiffness tether 1101 is depicted in FIG. 11A. The proximal portion 1102 and the distal portion 1104 may each have longitudinal lumens 1103a, 1103b. Attachment mechanism 1100 may comprise a first clasp 1106 and a second clasp 1108, where the first and second clasps are sized and shaped to engage each other. For example, the first and second clasps may be shaped to interfit with each other along at least the longitudinal axis of the tether 1101. The first and second clasps 1106, 1108 may each have longitudinal lumens 1107a, 1107b, where the longitudinal lumens 1107a, 1107b such that when the clasps are engaged, the lumens are aligned. Engagement of the first and second clasps 1106, 1108 may also align the longitudinal lumens 1103a, 1103b of the proximal and distal portion of the tether 1101. The attachment mechanism 1100 may also comprise a pull-wire 1105 that is slidable within the longitudinal lumens 1103a, 1103b, 1107a, and 1107b. When the first and second clasps 1106, 1108 are engaged, the pull-wire 1105 may slidably extend within the lumen 1103a of the proximal portion 1102, through the first clasp 1106, through the second clasp 1108, and into the lumen 1103b of the distal portion 1104. When the pull-wire 1105 extends from the proximal portion 1102, through the attachment mechanism 110, and into the distal portion 1104, it may act to secure the engagement of the first and second clasps such that the proximal and distal portions are connected and/or coupled together. Advancing the pull-wire 1105 to this configuration may act to secure the proximal and distal portions together. To release the proximal and distal portions from each other, the pull-wire 1105 may be retracted from the lumen 1103b of the distal portion 1104 and the lumen 1107b of the second clasp 1108. This may allow the first and second clasps to disengage from each other, thereby releasing the proximal portion from the distal portion.

Figure 11B:
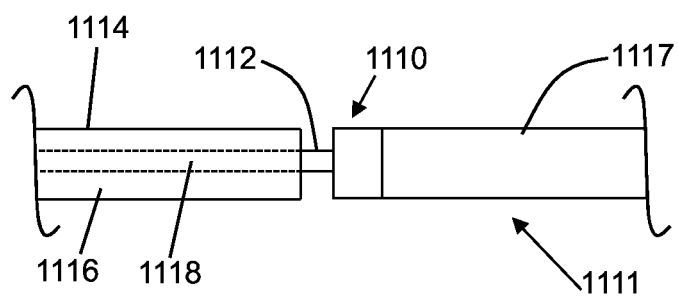

Another variation of an attachment mechanism 1110 between a rigid proximal portion 1114 and a flexible distal portion 1117 of a variable stiffness tether 1111 is depicted in FIG. 11B. Attachment mechanism 1110 may be a sacrificial junction that comprises a segment 1112 made of a material that dissolves or weakens upon the application of heat and/or increase in temperature. For example, the segment 1112 may comprise a temperature-sensitive polymer (e.g., a thermoplastic) that dissolves or weakens when heated (e.g., polyethylene, polypropylene, polyamide, polyoxymethylene and the like) to temperatures between about 50° C. to about 260° C. (e.g., about 50° C., 100° C., 200° C., etc.). Alternatively or additionally, the segment 1112 may comprise an ionized metal that dissolves or weakens when heated (any metal that is subject to galvanic corrosion, such as steel and the like) to temperatures between about 100° C. to about 850° C. The segment 1112 may be heated by any suitable fashion, for example, by resistive heating, and may be heated for short (e.g., 10 seconds or less) or prolonged (e.g., more than 10 seconds) periods of time. The rigid proximal portion 1114 may comprise an insulated outer layer 1116 surrounding a conductive core wire 1118. The core wire 1118 may contact the segment 1112. Heating the core wire 1118 from a proximal end of the tether 1111, and the heat may be conducted through the core wire 1118 to heat the segment 1112. In some variations, an electrical current (e.g., supplied by a power source at a proximal end of the tether) may be applied to the core wire 1118, which may provide sufficient resistive heating to dissolve and/or weaken the segment 1112. After the segment 1112 is heated sufficiently and has dissolved and/or weakened, the proximal portion may then be released from the distal portion (e.g., by applying a slight pulling or pushing force).

Figure 11C:
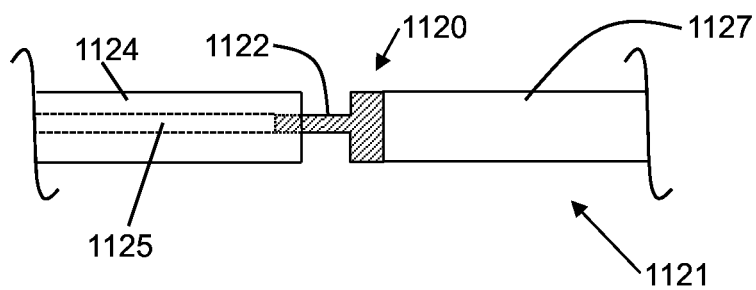

FIG. 11C depicts another variation of an attachment mechanism 1120 between a rigid proximal portion 1124 and a flexible distal portion 1127 of a variable stiffness tether 1121. Attachment mechanism 1120 may comprise a plug 1122 that is attached the proximal end of the distal portion 1127. The proximal portion 1124 may comprise a longitudinal lumen 1125 that is sized to frictionally engage the plug 1122. In some variations, the proximal portion 1124 may be a hypotube. Insertion of the plug 1122 into the lumen 1125 may act to engage the proximal and distal portions of the tether 1121. While plug 1122 may be fully inserted into the lumen 1125 to ensure a secure friction-fit, in some variations, inserting the plug partially within the lumen may provide a sufficient frictional force to ensure a secure attachment between the rigid proximal portion 1124 and the flexible distal portion 1127. To separate the proximal portion 1124 from the distal portion 1127, a pressure source (not shown) at a proximal end of the tether 1121 may apply a pulse of positive pressure (e.g., hydraulic pressure) to force the plug 1122 out of the lumen 1125. In some variations, the plug 1122 may be pushed out of the lumen 1125 with a push rod or other such actuator.

Figure 11D:
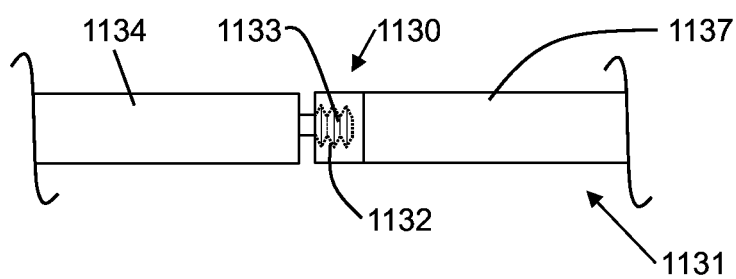
Figure 11E:
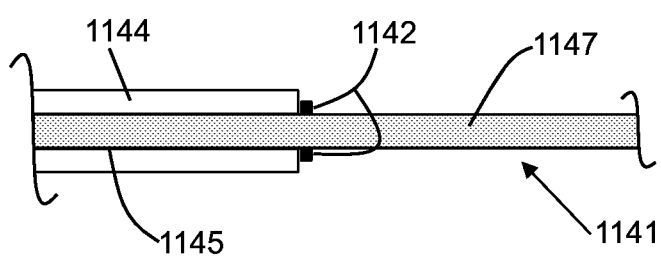
FIG. 11E depicts another variation of a variable stiffness tether.

FIG. 11D depicts another variation of an attachment mechanism 1130 between a rigid proximal portion 1134 and a flexible distal portion 1137 of a variable stiffness tether 1131. The screw-fit type attachment mechanism 1130 may comprise an internal thread 1132 attached to the proximal end of the distal portion 1137 and an external thread 1133 attached to the distal end of the proximal portion 1134. The proximal portion 1134 may be rotated in a first direction to engage the external thread 1133 with the internal thread 1132 (thereby connecting the proximal portion 1134 with the distal portion 1137) and may be rotated in a second direction opposite to the first direction to disengage the external thread from the internal thread (thereby disconnecting the proximal portion from the distal portion).

As described previously, a cutting instrument may be used to separate a rigid proximal portion from a flexible distal portion. A variable stiffness tether 1141 may comprise a rigid proximal portion 1144 with a longitudinal lumen 1145 therethrough, and a flexible portion 1147 with one or more stop members 1142 located at a length thereon. The flexible portion 1147 may slidably reside within the longitudinal lumen 1145, and in some variations, may be longer than the proximal rigid portion. In some variations, the rigid proximal portion 1144 may be distally advanced over the flexible portion until it contacts the stop member(s) 1142, which may prevent it from being further advanced. The flexible portion 1147 may be pulled proximally (e.g., to cinch a tethered anchor assembly), which may cause the distal end of the proximal portion 1144 to press against the stop(s) 1142. When a desired level of tension is applied and locked on the flexible portion 1147, a cutting instrument as previously described may be used to cut the flexible portion 1147. The portion of the flexible portion that is proximal to the cut may then be withdrawn proximally along with the rigid portion 1144.

In some variations, the flexible distal portion of a variable stiffness tether may be part of a tethered anchor assembly, where a plurality of anchors are coupled to the tether. While the distal-most anchor may be fixed attached to the tether, the remaining proximal anchors may be slidably coupled to the tether such that tension applied to the tether may cinch the anchor assembly. In some variations, the attachment mechanism may be sized and shaped such that a tether-locking device may be advanced over it to secure the tension in the tether. The attachment mechanism may also be sized and shaped to pass through an eyelet of a tissue anchor. The location of the attachment mechanism along a variable stiffness tether vary as the tether is used to deliver devices and/or to tension an anchor assembly coupled thereon. The location of the attachment mechanism prior to the application of tension to the tethered anchor assembly may be within the patient's body, for example, distal to the proximal-most anchor of the tethered anchor assembly. Once tension is applied to the tether (e.g., by pulling the tether proximally), the attachment mechanism may be located proximal to the proximal-most anchor of the tethered anchor assembly. In still other variations, the attachment mechanism may be located outside of the patient's body throughout the entire procedure. In another variation, the attachment mechanism may be located within the patient's body during a portion of the procedure (e.g., before tension is applied to the tether) and located outside the patient's body during another part of the procedure (e.g., after tension is applied to the tether).

Figure 9A:
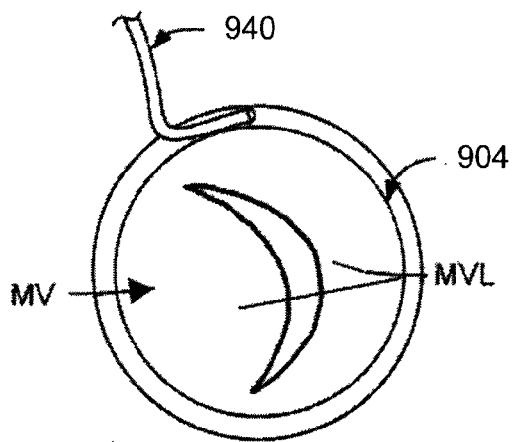
FIGS. 9A to 9I schematically depict an embodiment of a method of delivering multiple tissue anchors to annular tissue and cinching the anchors to tighten the annular tissue, using an embodiment of a tether with a flexible distal portion and a stiff proximal portion.
Figure 9B:
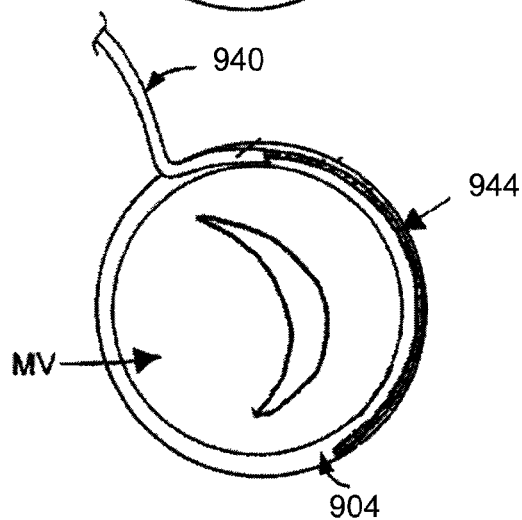
Figure 9C:
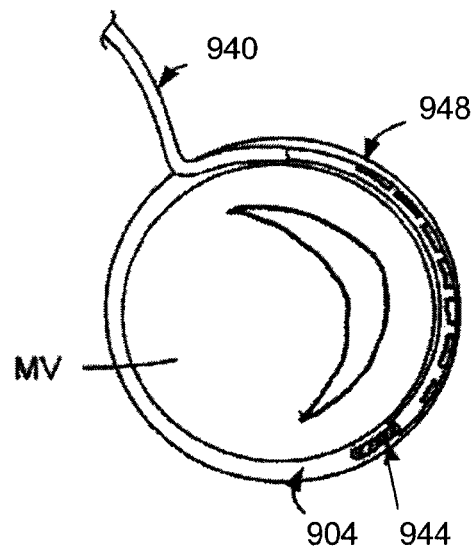
Figure 9D:
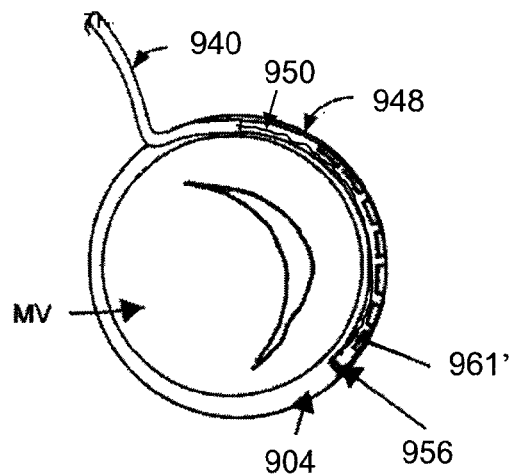
Figure 9E:
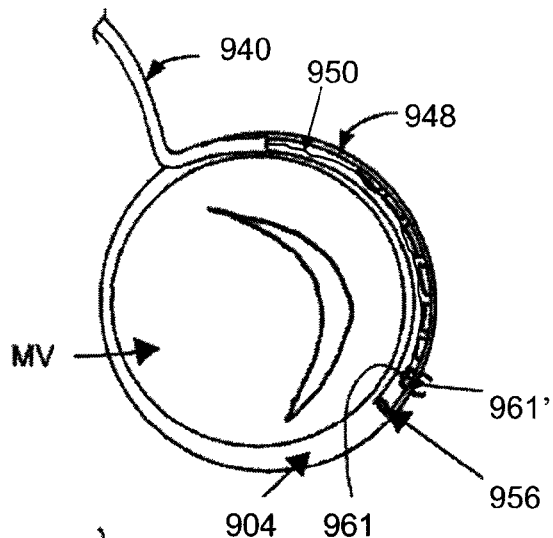
Figure 9F:
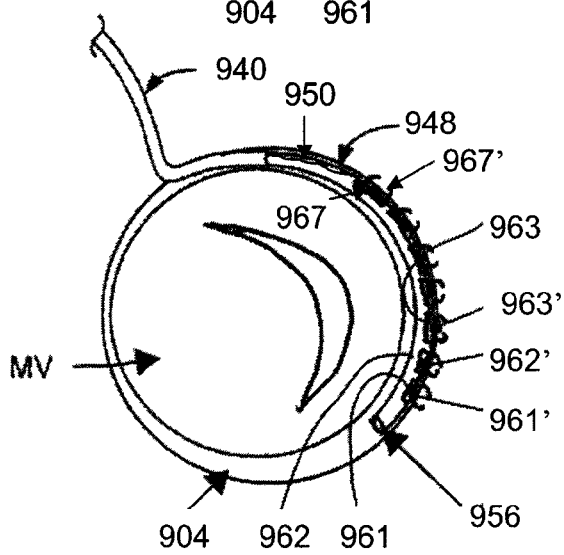
Figure 9G:
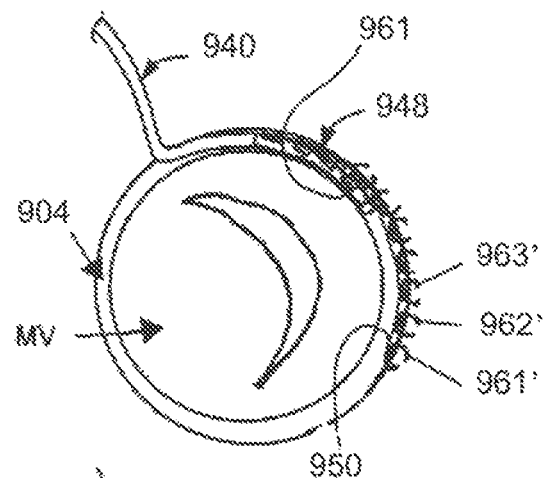
Figure 9H:
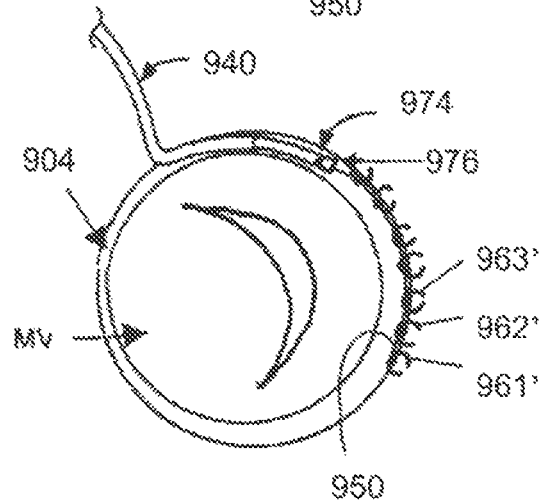
Figure 9I:
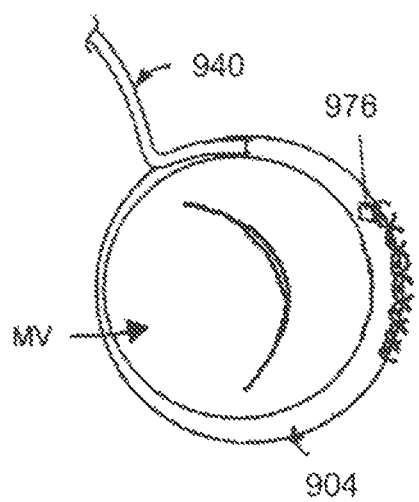

FIGS. 9A to 9I schematically depict a method of delivering multiple tissue anchors using one embodiment of a tether with variable stiffness. As illustrated in FIG. 9A, a guide catheter 940 is used to access a subvalvular region 904 of a mitral valve (MV) in order to augment the function of the mitral valve leaflets (MVL). A guidewire 944 is then passed through guide catheter 940 and along subvalvular region 904 as shown in FIG. 9B. After guidewire 940 reaches a target site, a multi-window tunnel catheter 948 is passed down guidewire 944 as illustrated in FIG. 9C. In one embodiment, tunnel catheter 948 is a releasable multi-window tunnel catheter as described in one or more embodiments of U.S. patent application Ser. No. 12/366,553 and filed on Feb. 5, 2009, entitled "Multi-Window Guide Tunnel", which is incorporated by reference in its entirety. As shown in FIG. 9D, after guidewire 944 is removed from tunnel catheter 948, a delivery catheter (not shown) carrying one deployable anchor 961' coupled to a tether 950 may be advanced through the lumen of tunnel catheter 948 and toward a side window 961 near the distal tip 956 of tunnel catheter 948. Tether 950 may be any of the embodiments described above. It may comprise a flexible distal portion, the length of which is suitable for this particular medical procedure (i.e., to cinch a plurality anchors that are engaged in annular tissue to tighten the annular tissue.) After the anchor 961' is deployed through window 961 and self-secures into the annular tissue accessible from the subannular groove region 904, the delivery catheter (again not shown) is then proximally withdrawn, as depicted in FIG. 9E. Another delivery catheter (still not shown) carrying another deployable anchor 962' is then passed down tether 950 and deploys the second anchor 962' through a second side window 962. Once anchor 962' exits window 962 and engages the annular tissue, the delivery catheter is again proximally withdrawn. In this fashion, multiple anchors 961' to 967' (e.g., anchor 963') are serially deployed individually by delivery catheters through multiple side windows 961 to 967 (e.g., window 963) on the tunnel catheter 948 as shown in FIG. 9F. With reference to FIG. 9G, after all of anchors 961' to 967' have been deployed, tunnel catheter 948 is proximally withdrawn from guide catheter 940. In FIG. 9H, a termination catheter 974 is introduced to facilitate tensioning of tether 950, thereby cinching anchors 961' to 967' together to remodel the annular tissue. In some embodiments, termination catheter 974 can also be used to separate the flexible distal tether portion from tether 950. For example, if the embodiment of the tether as shown in FIG. 1 is used here, termination catheter 974 is first passed down tether 100. A locking member 976 located in termination catheter 974 in FIGS. 9H and 9I can then be used to engage tether 100 near a location 105 where the flexible distal tether portion 101 is joined by the stiff proximal tether portion 102. A cutting member (not shown) located in termination catheter 974 is then used to cut off the distal tether portion 101 from tether 100. In some embodiments, locking member 976 remains in the blood vessel with the distal tether portion 101 and resists tether 101 loosening or slippage, as illustrated in FIG. 9I. Once the stiff proximal tether portion 102 is cut off, it can be proximately withdrawn with termination catheter 974. Devices and methods for performing termination of cinchable implants (e.g., the tether) are described in more detail in U.S. patent Ser. No. 12/253,885, which has already been incorporated by reference in its entirety.

While this invention has been particularly shown and described with references to embodiments thereof, it will be understood by those skilled in the art that various changes in form and details may be made therein without departing from the scope of the invention. For all of the embodiments described above, the steps of the methods need not be performed sequentially.

What is claimed is:

1. A guidewire element comprising:
   a rigid proximal portion;
   a flexible distal tether portion that is less rigid than the proximal portion;
   an attachment portion located between the flexible distal tether portion and the rigid proximal portion that releasably attaches the flexible distal tether portion to the rigid proximal portion; and
   wherein the flexible distal tether portion is configured to be used as a tensioning element and to be detached after tensioning.

2. The guidewire element of claim 1, wherein the flexible distal tether portion has a first torsional stiffness and the rigid proximal portion has a second torsional stiffness that is higher than the first torsional stiffness.

3. The guidewire element of claim 1, wherein a yield force of the rigid proximal portion as determined by compression testing is greater than a yield force of the flexible distal tether portion as determined by compression testing.

4. The guidewire element of claim 1, wherein the rigid proximal portion comprises a first portion and a second portion, wherein the first portion is more rigid than the second portion.

5. The guidewire element of claim 1, wherein the attachment portion comprises a first clasp attached to the rigid proximal portion, a second clasp that interfits with the first clasp attached to the flexible distal tether portion, and a pull-wire slidably insertable within the first and second clasps, wherein in a first protracted configuration the pull-wire secures the engagement between the first and second clasps, and in a second retracted configuration the pull-wire releases the engagement between the first and second clasps.

6. The guidewire element of claim 1, wherein the attachment portion comprises a temperature-sensitive polymer segment that is attached between the rigid proximal portion and the flexible distal tether portion, wherein the temperature-sensitive polymer segment is configured to weaken when heated.

7. The guidewire element of claim 1, wherein the attachment portion comprises a metal segment that is attached between the rigid proximal portion and the flexible distal tether portion, wherein the metal segment is configured to weaken when heated.

8. The guidewire element of claim 7, wherein the attachment portion comprises a metal segment susceptible to electrolytic dissolution that is attached between the rigid proximal portion and the flexible distal tether portion, wherein the metal segment is configured to dissolve when subjected to an electrical charge.

9. The guidewire element of claim 1, wherein the attachment portion comprises a plug attached to the flexible distal tether portion, wherein the rigid proximal portion comprises a lumen that is sized and shaped to frictionally retain the plug.

10. The guidewire element of claim 1, wherein the attachment portion comprises a screw joint, wherein the external thread of the screw joint is attached to the rigid proximal portion and the internal thread of the screw joint is attached to the flexible distal tether portion.

11. The guidewire element as in claim 1, wherein the flexible distal tether portion and the rigid proximal portion are made from a same material and said rigid proximal portion is stiffened by applying a stiffening agent.

12. The guidewire element as in claim 11, wherein the material is biodegradable.

13. The guidewire element as in claim 11, wherein the material is non-biodegradable.

14. The guidewire element as in claim 1, wherein the flexible distal tether portion is in the range of from about 5 cm to about 30 cm in length.

15. The guidewire element as in claim 1, wherein a ratio of the axial length of the flexible distal tether portion to the axial length of the rigid proximal portion is in the range of from about 0.05 to about 0.5.

16. The guidewire element as in claim 1, wherein the flexible distal tether portion is a monofilament and the rigid proximal portion is braided.

17. The guidewire element as in claim 1, wherein the flexible distal tether portion is braided and the rigid proximal portion is monofilament.

18. The guidewire element as in claim 1, wherein the rigid proximal portion comprises a larger outer diameter than the flexible distal tether portion.

19. The guidewire element as in claim 1, wherein the flexible distal tether portion is made from a first material; wherein the rigid proximal portion comprises at least one filament, and wherein the filament is made from a second material stiffer than the first material.

20. The guidewire element as in claim 1, wherein the flexible distal tether portion and the rigid proximal portion are coated with different materials.

* * * * *